(12) United States Patent
Boday et al.

(10) Patent No.: US 11,890,342 B2
(45) Date of Patent: Feb. 6, 2024

(54) STIMULUS-RESPONSIVE MICELLAR CARRIER

(71) Applicants: International Business Machines Corporation, Armonk, NY (US); Agency for Science, Technology, and Research (ASTAR), Singapore (SG)

(72) Inventors: Dylan J. Boday, Tucson, AZ (US); Jeannette M. Garcia, San Leandro, CA (US); James L. Hedrick, Pleasanton, CA (US); Nathaniel Park, San Jose, CA (US); Rudy J. Wojtecki, San Jose, CA (US); Yang Chuan, The Nanos (SG); Ashlynn Lee, The Nanos (SG); Zhen Chang Liang, The Nanos (SG); Shaoqiong Liu, The Nanos (SG); Yi Yan Yang, The Nanos (SG)

(73) Assignee: International Business Machines Corporation, Armonk, NY (US)

( * ) Notice: Subject to any disclaimer, the term of this patent is extended or adjusted under 35 U.S.C. 154(b) by 237 days.

(21) Appl. No.: 17/130,415

(22) Filed: Dec. 22, 2020

(65) Prior Publication Data
US 2021/0145970 A1    May 20, 2021

Related U.S. Application Data

(62) Division of application No. 15/479,071, filed on Apr. 4, 2017, now Pat. No. 11,045,552.

(51) Int. Cl.
*A61K 47/34* (2017.01)
*A61K 9/00* (2006.01)
(Continued)

(52) U.S. Cl.
CPC ............ *A61K 47/34* (2013.01); *A61K 9/0019* (2013.01); *A61K 9/107* (2013.01);
(Continued)

(58) Field of Classification Search
None
See application file for complete search history.

(56) References Cited

U.S. PATENT DOCUMENTS

| 8,546,488 B2 | 10/2013 | Thayumanavan et al. |
| 8,916,697 B2 | 12/2014 | Thompson et al. |

(Continued)

OTHER PUBLICATIONS

Li et al. (Acetal linked polymeric prodrug micelles for enhanced curcumin delivery), Colloidal and Surface B: Biointerfaces 140 (2016) 11-18. (Year: 2016).

Kalva et al. "Controlled micellar disassembly of photo-and pH-cleavable linear-dendritic block copolymers", Polymer Chemistry, 6. 6825-6835. (Year: 2015).

(Continued)

*Primary Examiner* — Isis A Ghali
(74) *Attorney, Agent, or Firm* — Patterson + Sheridan, LLP (57) ABSTRACT

A stimulus-responsive micellar carrier, methods that may be associated with making a stimulus-responsive micellar carrier, and methods that may be associated with using a stimulus-responsive micellar carrier are disclosed. The stimulus-responsive micellar carrier comprises a cargo molecule, and a linear block copolymer having a hydrophilic block connected to a hydrophobic block by a stimulus-responsive junction moiety. The micellar carrier can be supplied to a patient body for therapeutic purposes, such as the treatment of cancerous tissue. A method of preparing or obtaining a stimulus-responsive micellar carrier may include preparing a polyethylene glycol material having an acetal end group and then preparing a block copolymer by forming a reaction mixture including the polyethylene glycol material, a cyclic carbonate monomer, and a base.

18 Claims, 5 Drawing Sheets

(51) Int. Cl.
*A61K 9/107* (2006.01)
*A61K 38/00* (2006.01)
*A61K 31/7088* (2006.01)
*C08G 64/18* (2006.01)
*A61K 47/10* (2017.01)

(52) U.S. Cl.
CPC .......... *A61K 31/7088* (2013.01); *A61K 38/00* (2013.01); *A61K 47/10* (2013.01); *C08G 64/183* (2013.01)

(56) References Cited

U.S. PATENT DOCUMENTS

| | | |
|---|---|---|
| 2006/0127925 A1 | 6/2006 | Stayton et al. |
| 2009/0246167 A1 | 10/2009 | Zion et al. |
| 2011/0269814 A1 | 11/2011 | Manoharan et al. |
| 2012/0100079 A1 | 4/2012 | Burdinski et al. |
| 2013/0011362 A1 | 1/2013 | Monahan et al. |
| 2014/0271885 A1 | 9/2014 | Sill et al. |
| 2017/0319704 A1* | 11/2017 | Chin .................... A61K 9/0019 |

OTHER PUBLICATIONS

"List of IBM Patents or Patent Applications Treated as Related," for U.S. Appl. No. 17/130,415, filed Dec. 22, 2020.

U.S. Appl. No. 15/479,071, "Stimulus-Responsive Micellar Carrier," filed Apr. 4, 2017.

Chen et al. "PH-Responsive Biodegradable Micelles Based on Acid-Labile Polycarbonate Hydrophobe: Synthesis and Triggered Drug Release", Biomacromolecules 2009, 10, 1727-1735. (Year: 2009).

Gaucher et al. "Polyester-based micelles and nanoparticles for the parenteral delivery of taxanes", Journal of Controlled Release 143 (2010) 2-12. (Year: 2010).

Kataoka et al. "Block copolymer micelles for drug delivery: Design, characterization and biological significance", Advanced Drug Delivery Review 64 (2012), 37-48. (Year: 2012).

Lee et al. "Poly(L-histidine)-PEG block copolymer micelles and pH-induced stabilization", Journal of Controlled Release 90 (2003) 363-37 4. (Year: 2003).

Yang, et al. "The role of non-covalent interactions in anticancer drug loading and kinetic stability of polymeric micelles", Biomaterials 33 (Apr. 2012).

* cited by examiner

STIMULUS-RESPONSIVE MICELLAR CARRIER

CROSS-REFERENCE TO RELATED APPLICATIONS

This application is a divisional of co-pending U.S. patent application Ser. No. 15/479,071, filed Apr. 4, 2017. The aforementioned related patent application is herein incorporated by reference in its entirety.

BACKGROUND

The present disclosure relates, in general, to polymeric micelles with applications as carriers or delivery vehicles for therapeutic agents or other small molecule cargo.

Polymeric micelles are considered promising carriers for therapeutic agents in medical applications. Several types of polymer micelles have already been used in hospital settings or have been investigated in clinical trials. Micelles are aggregates of certain molecules that have portions that are mutually attracted to each other. For example, polymeric chains having a hydrophobic end (tail) and a hydrophilic end (head) can aggregate, after an initial dispersal in a liquid, into nanostructured micelles via supramolecular interactions. A polymer including a hydrophobic block and a hydrophilic block may be referred to as an amphiphilic block copolymer. In general, amphiphilic block copolymers may spontaneously self-assemble into core-shell micelles in aqueous solutions when at a concentration above a critical concentration level (the critical micelle concentration or CMC). The resulting micelle has hydrophilic exterior (shell) and a hydrophobic interior (core). Typical sizes of such micelles are on the order of a few nanometers to several hundred nanometers in diameter.

A micelle formed with an amphiphilic block copolymer can be "loaded" with a hydrophobic cargo during the assembly process. That is, a cargo, such as a hydrophobic small molecule, will tend to segregate into the hydrophobic core of the micelle. A micelle assembly incorporating a cargo in association with its core region may be referred to as a carrier or, more particularly, a micellar carrier. In some instances, depending on dimension, such a micellar carrier may be referred to as a nanocarrier, a nanoparticle, or a cargo delivery vehicle.

When a drug or therapeutic agent is "loaded" as cargo into a hydrophobic core of the micelle, the hydrophilic shell can serve to protect the drug/agent during transport to an intended target site within a patient such as a tumor or other diseased tissue site. However, a controlled delivery or release of the cargo from the protected core region specifically at the intended target site is difficult to achieve. Furthermore, the therapeutic cargo will, in general, be less effective at the target site while still surrounded by the protective outer shell. Thus, it is usually preferable for the cargo to be released from the carrier at the target site if possible.

BRIEF SUMMARY

According to an embodiment of the present disclosure, a method comprises obtaining a micellar carrier that includes a block copolymer having a hydrophilic block connected to a hydrophobic block by a stimulus-responsive junction moiety and a cargo molecule. The method further includes supplying the micellar carrier to a patient body. In some examples, the cargo molecule may be a therapeutic agent. In some examples, the stimulus-responsive junction moiety may include an acetal linkage.

According to another embodiment of the present disclosure, a method includes preparing a polyethylene glycol material having an acetal end group and then preparing a block copolymer by forming a reaction mixture including the polyethylene glycol material, a cyclic carbonate monomer, and a base. In some examples, the base may be an organobase, such as DBU (diazabicycloundecene) or the like. The polyethylene glycol material may be derived from a linear polyethylene glycol in some examples.

According to still another embodiment of the present disclosure, a micellar carrier comprises a block copolymer having a hydrophilic block connected to a hydrophobic block by a stimulus-responsive junction moiety, and a cargo molecule that is hydrophobic. In some examples, the micellar carrier can be a nanocarrier. In some examples, the cargo molecule can be a therapeutic agent and the block copolymer may correspond the following chemical formula:

wherein n and m correspond to respective number of repeat units in the block copolymer.

Various example embodiments will be described with reference to the accompanying figures. The figures are schematic and/or conceptual and, unless otherwise noted, depictions are not intended to be at scale.

DETAILED DESCRIPTION

Micellar nanocarriers have been investigated as delivery vehicles for therapeutic agents for medical applications. In general, a micellar nanocarrier is formed to incorporate drug molecules, therapeutic agents, or the like as cargo that is loaded in to the nanocarrier's core. The nanocarrier incorporating the cargo can then be administered to a patient by various possible means, such as orally, intravenously, subcutaneously, etc. The nanocarrier protects the cargo from degradation in and/or elimination from the patient's body. In cases when, for example, the cargo has high toxicity, the nanocarrier may also act to protect the patient from adverse or unintended effects of the cargo being released non-specifically within the body. Preferably, a high toxicity cargo might only be released into the body at specific diseased sites rather than broadly or non-specifically to all parts of the body.

Amongst many advantages, a targeted cargo release from a micellar carrier allows for smaller total amounts of cargo to be supplied to a patient since it is unnecessary to dose the patient's entire body volume to achieve therapeutic concentrations at the diseased site. Likewise, targeted release could limit damage that otherwise might be caused to healthy tissue outside of the target site(s) that could be attendant to a general release of the cargo within the patient. The present disclosure describes methods and materials by which targeted release of therapeutic cargos can be achieved using core-shell micelles as nanocarriers.

Figure 1:
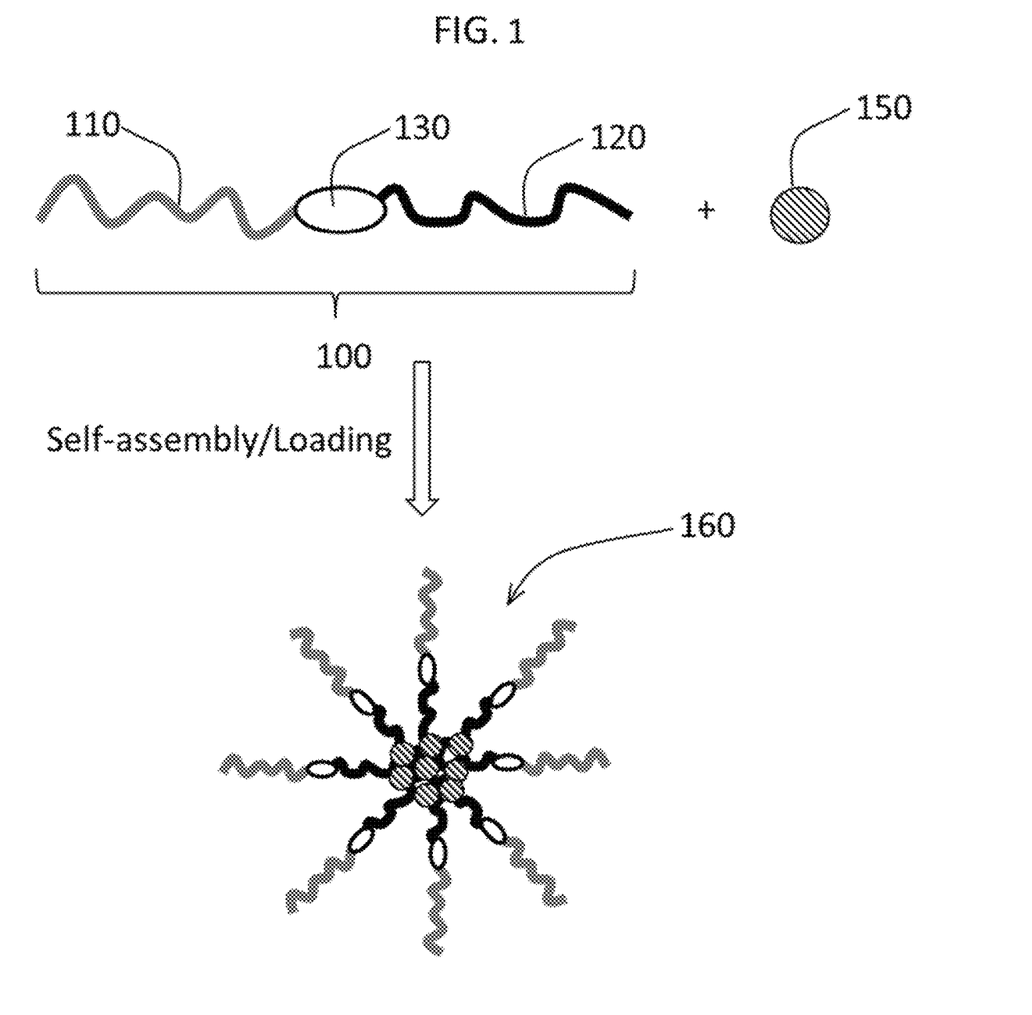
FIG. 1 depicts a general scheme for preparing core-shell micelle for drug or therapeutic agent delivery.

With reference now to FIG. 1, a scheme for preparing a core-shell micelle for drug or therapeutic agent delivery is depicted. An amphiphilic linear block copolymer 100 is prepared to include a hydrophobic block and a hydrophilic block. In this example, the block copolymer 100 is a diblock polymer including a hydrophilic block 110 and a hydrophobic block 120. The hydrophilic block 110 is linked to the hydrophobic block 120 by a stimuli-responsive junction moiety 130.

Once synthesized, the block copolymer 100 can be mixed in an aqueous solution with a therapeutic agent 150, which in this instance is hydrophobic. When mixed in this manner, the block copolymer 100 and the therapeutic agent 150 aggregate or self-assemble into micelle 160. Micelle 160 may also be referred to as a nanoparticle or a nanocarrier in some contexts. The therapeutic agent 150 can comprise therapeutic molecules, drug compounds, proteins, DNA fragments, RNA fragments, and/or other molecules or compounds having bioactivity that might be used to treat diseases and/or conditions in a patient.

As depicted in FIG. 1, the core of micelle 160 is formed by the hydrophobic moieties (hydrophobic blocks) 120 of several block copolymers 100. The hydrophobic therapeutic agent(s) 150 (e.g., small molecules chemical compounds) can be loaded into core by supramolecular attractions between the hydrophobic components. Cargo loading capacity of polymeric micelle cargo carriers is mainly affected by the interactions between the cargo component(s) and the micellar core. As such, either or both of the therapeutic agent 150 or the hydrophobic blocks 120 may be tailored to adjust load capacity. For example, the length/size of the hydrophobic block 120 may be increased or decreased to alter load capacity. The shell of the micelle 160 is formed by the hydrophilic moieties (hydrophilic blocks) 110. The hydrophilic shell protects the therapeutic agent 150 associated with the core from chemical and biological attack such as enzymatic degradation, opsonization by phagocytes and macrophages, and the like.

Figure 2:
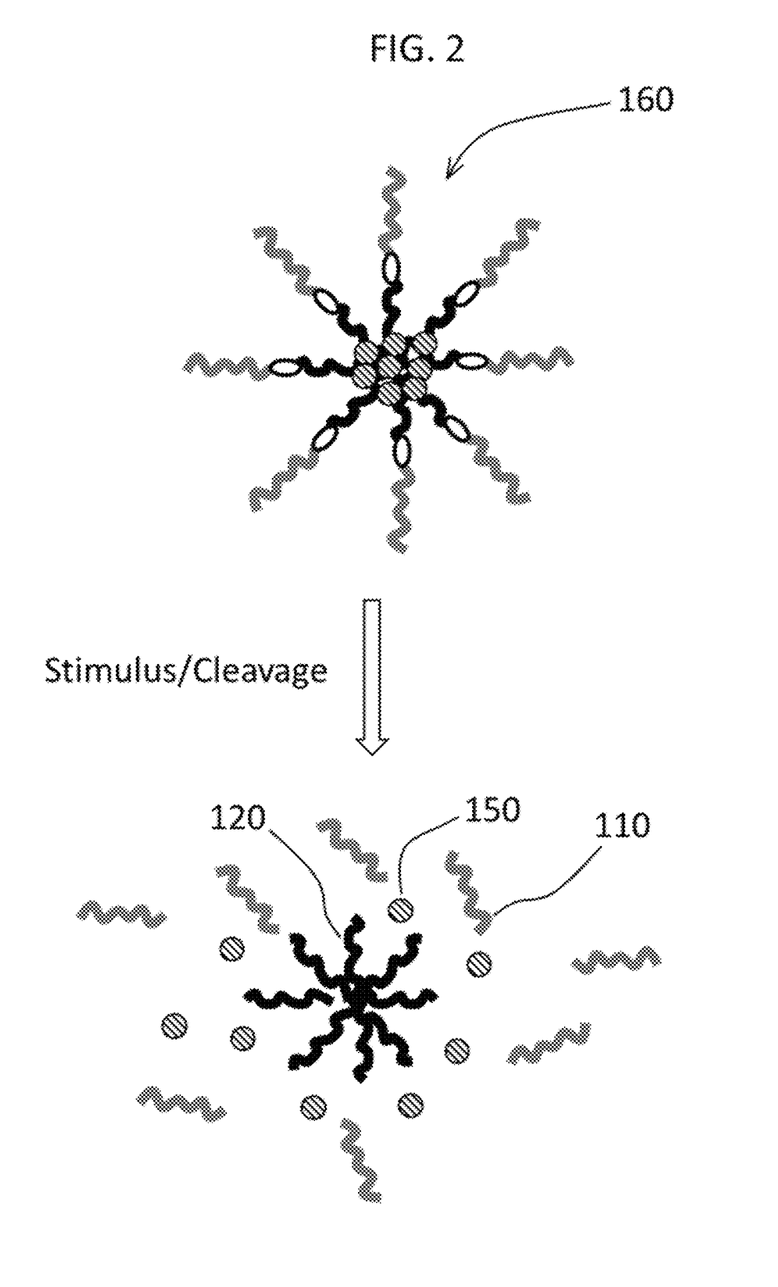
FIG. 2 depicts a triggered release of a core-shell micelle for drug or therapeutic agent delivery.

As depicted in FIG. 2, the stimuli-responsive junction moiety 130 responds to environmental changes by de-linking the hydrophobic block 120 from the hydrophilic block 110 of the micellar core region. That is, the response of the stimuli-responsive junction moiety 130 causes cleaving of the amphiphilic block copolymer 100 into its component blocks (e.g., blocks 110 and 120). The cleaving of the amphiphilic block copolymer 100 in effect destabilizes the micelle 160 and allows the outer shell (comprised of hydrophilic blocks 110) to disperse, leaving the core (comprised of hydrophobic blocks 120) unprotected or exposed.

FIG. 2 depicts the therapeutic agents 150 (previously loaded within the core region of micelle 160) as dispersing; however, such a physical dispersal of the therapeutic agent(s) 150 is not a requirement and "release" of the therapeutic agent(s) 150 in this context may, in some instances, consist only of an increase in exposure or availability of the therapeutic agents 150 that might accompany the release/dispersal of the shell of micelle 160. That is, therapeutic agent(s) 150 might remain aggregated with the remaining core of micelle 160 (the hydrophobic blocks 120) for an indefinite period of time after the cleaving of amphiphilic copolymer 100.

It should be noted that dimensions and relative ratios of dimensions for the sub-portions of micelle 160 depicted in FIG. 1 and FIG. 2 are not necessarily to scale for an actual micelle 160. The depicted dimensions of block copolymer 100 and therapeutic agent 150, along with the total number of block copolymers 100 and therapeutic agents 150, within micelle 160 have been selected for purposes of explaining the general arrangement of the various parts of micelle 160 rather than for dimensional or numerical correctness.

The total number (aggregation number) of block copolymers 100 within micelle 160 is not a limitation and may be any number that provides a micellar character to micelle 160. Likewise, the total number (loading) of the therapeutic agents 150 incorporated into micelle 160 is not a limitation and may be any number greater than one. It is also possible for micelle 160 to be provided for purposes of storage and/or therapeutic delivery in a mixture with other micelles or micellar materials that incorporate no therapeutic agent 150. Likewise, when more than one molecule of a therapeutic agent 150 is incorporated into a micelle 160, it is not a requirement that each such therapeutic agent 150 be the same-type of molecule or compound. That is, a mixture of different therapeutic agents 150 may be incorporated into each micelle 160. Similarly, a mixture of several different micelles 160 each having a different therapeutic agent may be prepared and then administered collectively. Furthermore, it is not necessarily required for the structure of micelle 160 to be composed exclusively of block copolymers 100. That is, other amphiphilic copolymers lacking a stimulus-responsive junction moiety 130 may be included in micelle 160 along with the block copolymers 100 to control or adjust release of the therapeutic agents 150 after the junction severing triggering stimulus has been encountered.

In general, though it is not necessarily a limitation, a micelle 160 may be a nanoscale (~$10^{-9}$ m) to microscale (~$10^{-6}$ m) particle. In some examples, the micelle 160 may have a diameter the range of 20 nm to 200 nm. In this context, diameter refers to a hydrodynamic dimension as measured, for example, by a light scattering method, such as static light scattering (SLS) or dynamic light scattering (DLS), under conditions (e.g., pH, temperature, concentration) corresponding to relevant biological conditions. In a particular embodiment, the volume-weighted average hydrodynamic diameter for a distribution of micelles 160 may be in the range of 20 nm to 200 nm for relevant biological environmental conditions.

In a particular embodiment, the stimuli-responsive junction moiety 130 is a pH-sensitive junction moiety. Thus, for this embodiment, the stimulus to which the stimuli-responsive junction moiety 130 responds includes a change in pH level of the micelle's surroundings. The pH-sensitive junction moiety in this particular embodiment can include an acetal group, which is stable under basic and neutral conditions (pH≥7), but degrades under acidic conditions (pH≤~6.5).

Thus, in aqueous media at a neutral or physiological pH level (pH=~7.4), such a block copolymer 100 can act as a surfactant and self-assemble into a core-shell nanoparticle (e.g., a spherical micelle) 160. During this self-assembly process, hydrophobic small molecules such as an anti-cancer drug (e.g., a therapeutic agent 150) can be incorporated into the micelle 160. In this context, micelle 160 may also be referred to as nanocarrier 160. This loaded nanocarrier 160 will be stable at neutral or physiological pH conditions, as long as its local concentration remains above the CMC. However, upon exposure to low pH conditions, the acetal group of the junction moiety 130 will degrade, cleaving the hydrophilic shell from of the nanocarrier 160, thereby releasing the cargo (e.g., therapeutic agent 150) loaded in the core of the nanocarrier 160.

Targeted Delivery

In micelle 160, the protective outer shell acts to increase, for example, the time the therapeutic agent 150 remains unaffected by the elimination mechanisms and defenses of the patient's body. In addition, when micelle 160 has a size (diameter) of 20 nm-200 nm, it is large enough to escape extravasation from normal vessel walls and avoid premature elimination via the kidneys, but is generally small enough to permeate through leaky blood vessels and/or stay within the tumor tissues having compromised lymphatic filtration. This effect is otherwise known as the enhanced permeation and retention (EPR) effect. Thus, in some example embodiments, micelle 160 has a diameter in a range of 20 nm to 200 nm to utilize the EPR effect. Targeted delivery strategies, such as those that utilize the EPR effect, help reduce systemic toxicity of intravenously supplied therapeutic agents.

On the cellular level, nano-sized polymeric micelles offer an endocytosis internalization pathway allowing for easy cellular uptake. This nano-sizing helps overcome multidrug-resistance problems that might be caused by drug efflux mechanisms. Despite the numerous advantages of micellar drug delivery, several unmet challenges still exist with respect to targeted delivery of therapeutic agents. For example, when a drug-loaded micelle reaches its target, the release of the cargo/payload needs to occur for the intended therapeutic effect to take place at maximum efficiency. In other words, if the payload or therapeutic agent is retained inside the protected micellar core at the target site, there may be little to no therapeutic activity caused by the cargo because it remains surrounded (encapsulated) by a protective outer shell of the micelle and thus substantially unavailable for purposes of biological activity.

Mechanisms for cargo release at specific targets sites generally require destabilization of the micelle in one form or another. For instance, when the micelle is comprised of biodegradable polymers, then one can expect diffusion-limited release kinetics of the cargo according to the biodegradation rate of the polymer(s) forming the micelle. But in many instances it may be preferable for cargo release to be triggered by a specific stimulus that is unique to (or at least more prevalent at) the target site. For example, it is known that the extracellular microenvironment of cancerous tissue is often more acidic (pH range ~6.5 to ~6.9) than that of healthy tissue (pH ~7.4). Thus, a cargo release triggered by a drop into the pH 6.5 to pH 6.9 range could be used to provide selective cargo release from the micellar carrier at a cancerous target site.

In a particular example, an amphiphilic polycarbonate-based block copolymer nanocarrier can be provided such that the micellar hydrophilic shell is discarded at low pH (such as in pH range 6.5 to 6.9), thereby facilitating a stimuli-responsive cargo release mechanism for therapeutic agent delivery to a diseased microenvironment within the body.

Figure 3:
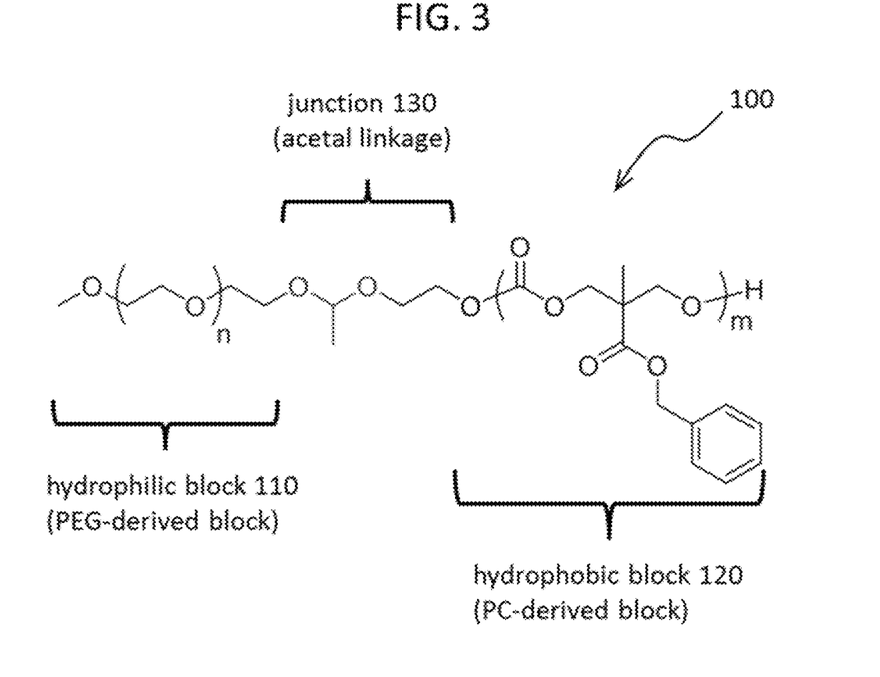
FIG. 3 depicts a block copolymer having a junction moiety which is stimuli responsive.

FIG. 3 depicts a particular example of an amphiphilic block copolymer 100. In this example, the hydrophilic block 110 is a polyethylene glycol (PEG) derived group, the hydrophobic block 120 is polycarbonate (PC) derived group, and the stimulus responsive junction moiety 130 is an acetal linkage. Many PEG materials are considered suitable for use in biomedical applications and the depicted polycarbonate material is considered biodegradable. Thus, various copolymers of PEG and PC could be expected to be suitable for certain biomedical applications, such as micellar nanocarriers.

Under acidic conditions, the acetal linkage in junction moiety 130 breaks down into acetaldehyde and the corresponding alcohols. Note also that ketal moieties can be used as junction moiety 130. Ketal moieties are similarly acid-sensitive as acetal moieties and have acetone and alcohols as decomposition products.

Though depicted as a linear polymer group, the PEG derived group may be branched or incorporate other morphologies. Other groups/polymers may be appended or grafted to PEG backbone of the PEG-derived group. The number of repeat units (n) in the PEG derived group may be varied in conjunction with the number of repeat units (m) of the PC derived group to provide an appropriate size for micelle 160.

In other examples, the hydrophilic block 110 can be a polypropylene glycol derived group or other polyether derived groups. Also, the amphiphilic block copolymer 100 is not limited to a diblock polymer and additional blocks may be incorporated in some instances while preserving micellar self-assembly by careful use of hydrophobic and hydrophilic components. In other examples, the PC derived group may have a structure corresponding to:

where R includes at least one carbon atom. In some examples, R may be one of a methyl group (—CH$_3$) or benzyl group (—CH$_2$C$_6$H$_5$). In other examples, R may be a derivate of a benzyl group, such as a benzyl group with a substituted benzene ring. In further examples, the R group may be an alkyl group, straight chain or branched, including 2 to 20 carbon atoms. The R group may incorporate a boronic acid functional group R$_1$—B(OH)$_2$, where R$_1$ includes an attachment to the PC derived group. R may include or be a urea (carbamide)-type functional group, (R$_1$R$_2$N)CO(NR$_3$R$_4$), in which one of R$_1$-R$_4$ includes an attachment to the PC derived group, and, in general, R$_1$-R$_4$ may otherwise independently be a hydrogen atom (H) or include at least one carbon. The R group may include or be a thiourea-type functional group, (R$_1$R$_2$N)CS(NR$_3$R$_4$), in which one of R$_1$-R$_4$ includes the attachment to the PC derived group, and, in general, R$_1$-R$_4$ may otherwise independently be a hydrogen atom (H) or include at least one carbon. In the above, R$_1$-R$_4$ may be alkyl groups including 1-20 carbons, and R$_1$-R$_4$ may include additional functional groups beyond those mentioned. The R group may incorporate one or more unsaturated groups, one or more cyclic groups, and one or more heterocyclic groups. In general, the structure of the R group should be consider limited only by any required synthetic compatibility with the preparation of the cyclic carbonate monomer and the ring-opening polymerization step (see FIG. 4B, described further below). It should be noted protection/de-protection of various functional groups which might be incorporated into the R group could be incorporated into the synthetic scheme when required.

Synthesis of Amphiphilic Block Copolymers

Figure 4A:
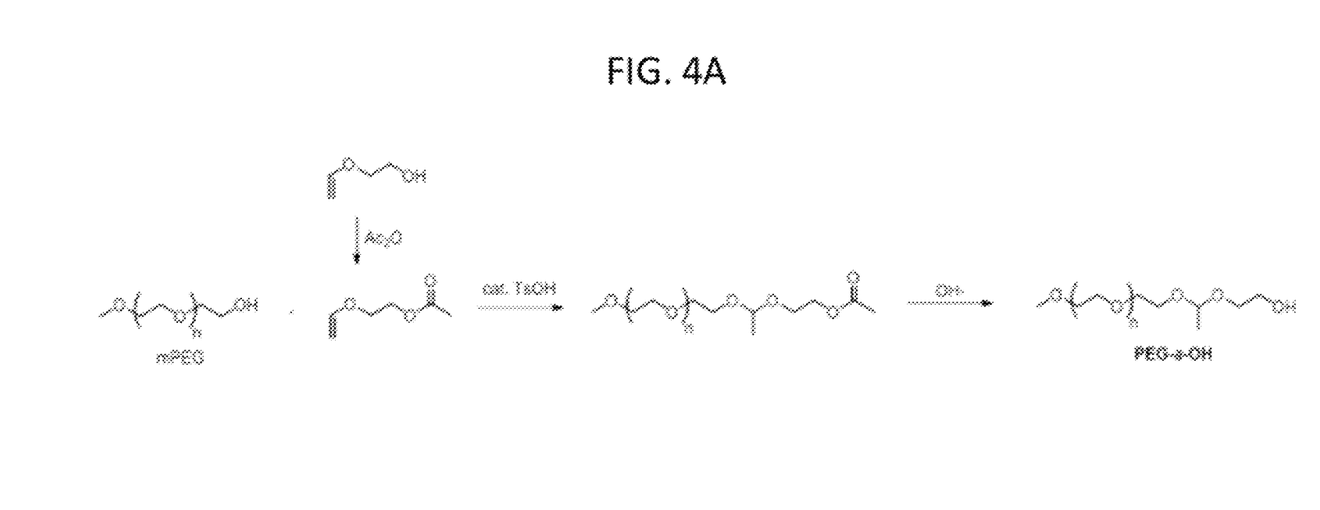
FIG. 4A depicts a synthesis of an acetal end-functionalized polyethylene glycol.

FIG. 4A depicts a synthesis process for an acetal end-functionalized polyethylene glycol. In particular, synthesis of one example acetal end-functionalized PEG (PEG-a-OH) is shown in FIG. 4A. The synthesis of PEG-a-OH is, in general, known. Here, a linear polyethylene glycol material (mPEG) is reacted with 2-(vinyloxy)ethyl acetate to form an intermediate PEG material having an acetate end group. The number (n) of repeat units in the mPEG may be any suitable number greater than one which provides sufficient hydrophilicity to the ultimate end product block copolymer to provide a micellar carrier 160 at the appropriate dimension. As depicted, this step utilizes a catalytic amount of p-toluene sulfonic acid (TsOH). Base catalyzed hydrolysis of the intermediate PEG material provides the PEG-a-OH material.

In FIG. 4A, the 2-(vinyloxy)ethyl acetate is depicted as being formed by the reaction of ethylene glycol vinyl ether (IUPAC: 2-(vinyloxy)ethanol) and acetic anhydride ($Ac_2O$). Other synthetic routes to PEG-a-OH are available and the process of FIG. 4A is provided as one possible route. Unless otherwise indicated, all chemical reactions described herein may be performed at ambient conditions or under mild heating in a suitable solvent.

Figure 4B:
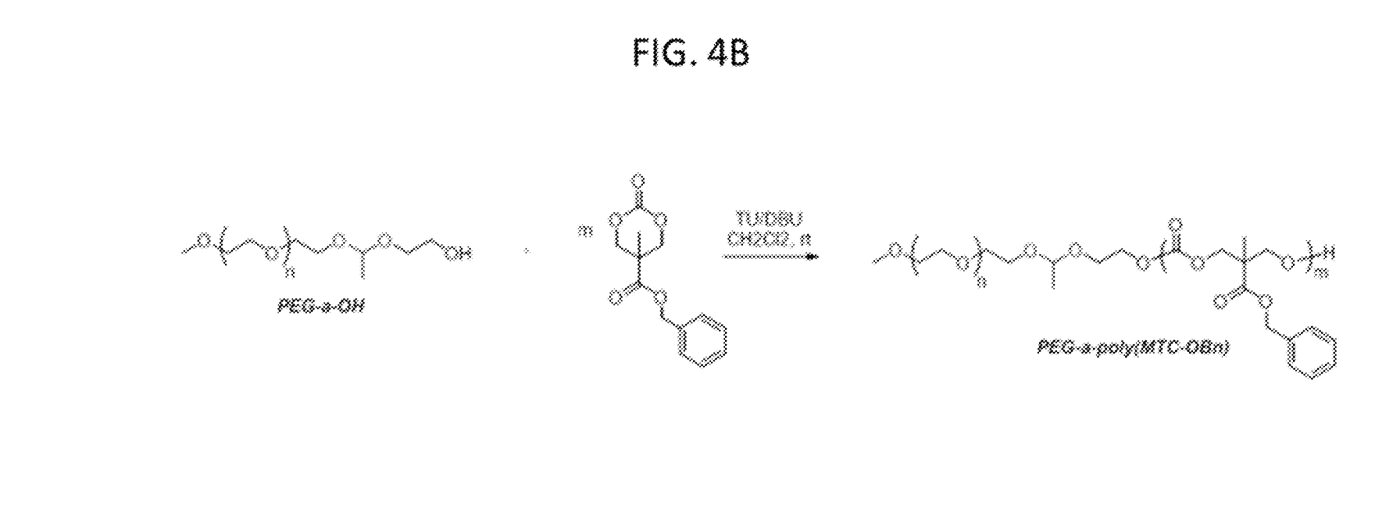
FIG. 4B a synthesis of a block copolymer having an acetal junction from an acetal end-functionalized polyethylene glycol.

FIG. 4B depicts the synthesis of a pH-sensitive block copolymer by DBU-catalyzed ring-opening polymerization (ROP) of a cyclic carbonate monomer (MTC-OBn) using PEG-a-OH (from FIG. 4A) as a polymerization initiator. Here, DBU (1,8-diazabicycloundec-7-ene) is an organobase that is non-nucleophilic. MTC-OBn is 2-benzyloxycarbonyl-2-methyltrimethylene carbonate. Here, the benzyl group is an example of the R group discussed in conjunction with explanation of the PC derived group above. In general, the benzyl group may be replaced in accordance with the description of the R group provided above.

Other bases with similar characteristics to DBU might be adopted in this context. A solvent, such as dichloromethane ($CH_2Cl_2$), is used in the reaction mixture. The reaction can be conducted at room temperature.

Figure 5:
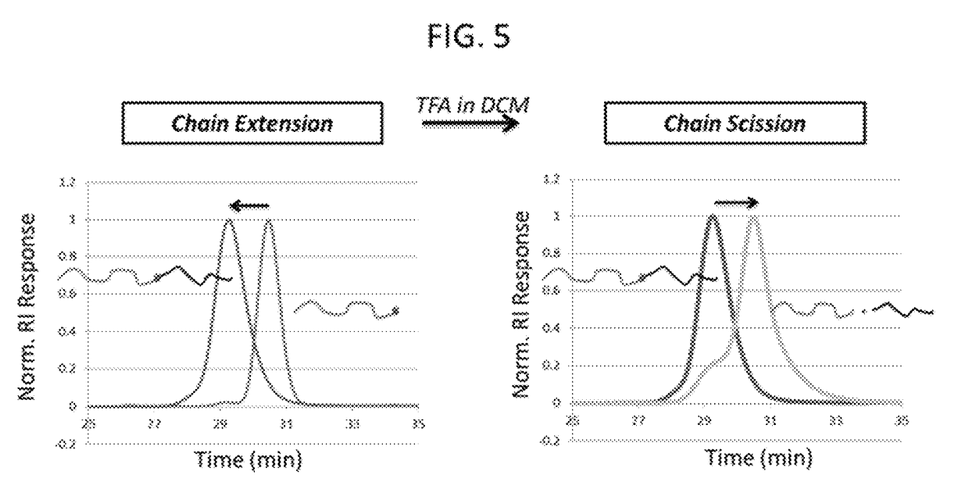
FIG. 5 depicts experimental results demonstrating (left side) linking of block copolymer having a stimuli-responsive junction moiety and (right side) pH-induced chain scissioning of the block copolymer having the stimuli responsive junction moiety.

The acetal functional group present in the PEG-a-OH material is compatible with the basic ROP conditions described here. Successful ROP to afford PEG-a-poly(MTC-OBn) was confirmed by gel permeation chromatography (GPC), as shown in FIG. 5 (left panel). The number (m) of repeat units of the carbonate group in the end product (PEG-a-poly(MTC-OBn) can be any suitable number greater than one which provides sufficient hydrophobicity to the end product block copolymer to provide a micellar carrier 160 at the appropriate dimensions.

As noted, successful formation of PEG-a-poly(MTC-OBn) is established by the shifting of GPC test peaks to shorter retention time (all other things being equal, larger molecules are retained for shorter times than smaller molecules) as shown in FIG. 5 (left side). The acid-induced degradation of PEG-a-poly(MTC-OBn) in an organic solvent is shown in FIG. 5 (right panel). Treating a dichloromethane ($CH_2Cl_2$) solution of the PEG-a-poly(MTC-OBn) with trifluoroacetic acid (TFA) at room temperature resulted in a significant loss in intensity of the GPC signal attributable to the block copolymer (at shorter retention times) and the appearance of a new signal shifted toward lower molecular weights (longer retention times). This result is consistent with cleavage of the block copolymer at the acetal junction.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for producing a linear block copolymer, comprising:
preparing an alcohol terminated polyethylene glycol (PEG) material having an acetal group, the preparation comprising:
reacting an alcohol terminated PEG with 2-(vinyloxy)ethyl acetate to form an acetate terminated PEG having the acetal group, and
hydrolyzing the acetate terminated PEG having the acetal group to form the alcohol terminated PEG material having the acetal group;
introducing the alcohol terminated PEG having the acetal group with a cyclic carbonate monomer; and
mixing the alcohol terminated PEG having the acetal group, the cyclic carbonate monomer, and a base to form a linear block copolymer, wherein the linear block copolymer consists of a hydrophilic block comprising a polyethylene glycol, a hydrophobic block having a structure comprising a carbonate group, and a stimulus-responsive junction moiety having the structure wherein one wavy bond represents a bond to the polyethylene glycol of the hydrophilic block and the other wavy bond represents a bond to the carbonate group of the hydrophobic block.

2. The method of claim 1, wherein the base is 1,8-diazabicycloundec-7-ene.

3. The method of claim 1, wherein the cyclic carbonate monomer has the following structure:

wherein R includes at least one carbon atom.

4. The method of claim 1, further comprising:
mixing the linear block copolymer with a cargo molecule to form a micellar carrier.

5. The method claim 4, further comprising:
supplying the micellar carrier to a patient body.

6. The method of claim 5, wherein supplying the micellar carrier is performed via intravenous injection.

7. A micellar carrier, comprising:
a linear block copolymer having a hydrophilic block comprising a polyethylene glycol and connected to a hydrophobic block by a stimulus-responsive junction moiety having the structure

, the linear block copolymer produced by the method of claim 1, and
a hydrophobic cargo molecule,
the hydrophobic block represented by:

wherein;
m is a numerical value greater than 1, and
R is selected from the group consisting of a benzyl group, an alkyl group, a boronic acid, a urea, and a hydrogen atom.

8. The micellar carrier of claim 7, wherein
the cargo molecule is a therapeutic agent, and
the linear block copolymer is represented by the following:

wherein n and m are independently a positive integer.

9. A micellar carrier, comprising:
a linear block copolymer comprising a hydrophilic block connected to a hydrophobic block by a stimulus-responsive junction moiety, wherein the hydrophilic block comprises a polyethylene glycol, the hydrophobic block comprises a carbonate group, and the stimulus-responsive junction moiety has the structure wherein one wavy bond represents a bond to the polyethylene glycol of the hydrophilic block and the other wavy bond represents a bond to the carbonate group of the hydrophobic block; and
a cargo molecule that is hydrophobic.

10. The micellar carrier of claim 9, wherein the micellar carrier has a diameter between 20 nm and 200 nm.

11. The micellar carrier of claim 9, wherein the cargo molecule is a therapeutic agent.

12. The micellar carrier of claim 9, wherein the cargo molecule is an anti-cancer compound.

13. The micellar carrier of claim 9, wherein a structure of the hydrophobic block further comprises an R group, wherein the R group is one of a methyl group, a benzyl group, a derivate of a benzyl group, a linear alkyl group having 2 to 20 carbon atoms, a branched alkyl group having 2 to 20 carbon atoms, a carbamide group having the chemical formula $(R_1R_2N)CO(NR_3R_4)$, or a thiourea group having the chemical formula $(R_1R_2N)CS(NR_3R_4)$, wherein each of $R_1$, $R_2$, $R_3$, and $R_4$ is independently a hydrogen or a group that includes at least one carbon atom.

14. The micellar carrier of claim 9, wherein a structure of the hydrophobic block further comprises an R group, wherein the R group includes a boronic acid functional group, a carbamide group having the chemical formula $(R_1R_2N)CO(NR_3R_4)$, a thiourea group having the chemical formula $(R_1R_2N)CS(NR_3R_4)$, one or more unsaturated groups, one or more cyclic groups, or one or more heterocyclic groups, wherein each of $R_1$, $R_2$, $R_3$, and $R_4$ is independently a hydrogen or a group that includes at least one carbon atom.

15. The micellar carrier of claim 9, wherein a structure of the hydrophobic block further comprises an R group, wherein the R group is one of a methyl group or a benzyl group.

16. The micellar carrier of claim 9, wherein the cargo molecule comprises protein.

17. The micellar carrier of claim 9, wherein the cargo molecule is a DNA fragment or RNA fragment.

18. The method of claim 1, wherein reacting the alcohol terminated PEG with 2-(vinyloxy)ethyl acetate to form the acetate terminated PEG having the acetal group further comprises using an acid catalyst.

* * * * *